US006995276B1

(12) United States Patent
Okubo et al.

(10) Patent No.: US 6,995,276 B1
(45) Date of Patent: Feb. 7, 2006

(54) CYCLIC DISULFIDE COMPOUND, PROCESS OF PRODUCING THE SAME AND OPTICAL PRODUCT COMPRISING THE SAME

(75) Inventors: Tsuyoshi Okubo, Tokyo (JP); Ken Takamatsu, Tokyo (JP)

(73) Assignee: Hoya Corporation, Tokyo (JP)

( * ) Notice: Subject to any disclaimer, the term of this patent is extended or adjusted under 35 U.S.C. 154(b) by 190 days.

(21) Appl. No.: 10/359,079

(22) Filed: Feb. 6, 2003

(30) Foreign Application Priority Data

Feb. 7, 2002 (JP) ............................. 2002-031293

(51) Int. Cl.
C07D 339/00 (2006.01)
C07D 327/06 (2006.01)
C07D 327/10 (2006.01)
C07D 341/00 (2006.01)

(52) U.S. Cl. ............................ 549/11; 549/14; 549/18; 549/19; 549/20; 549/30; 549/34; 549/35; 351/642

(58) Field of Classification Search ................. 549/11, 549/14, 18, 19, 20, 30, 34, 35; 351/642
See application file for complete search history.

(56) References Cited

U.S. PATENT DOCUMENTS

| 2,715,635 | A | * | 8/1955 | Davis ........................... 549/11 |
| 3,278,489 | A | | 10/1966 | Bernstein et al. |
| 3,503,758 | A | * | 3/1970 | Wada et al. ................ 426/535 |
| 3,631,158 | A | * | 12/1971 | Esclamadon et al. ....... 528/377 |
| 3,719,730 | A | | 3/1973 | Hansley et al. |
| 4,284,718 | A | | 8/1981 | Bergthaller et al. |
| 6,770,734 | B2 | * | 8/2004 | Tanaka et al. .............. 528/374 |

FOREIGN PATENT DOCUMENTS

| DE | 270 081 A1 | 7/1989 |
| EP | 0 435 306 A2 | 7/1991 |
| EP | 0 530 757 A1 | 3/1993 |
| EP | 0 562 966 A2 | 9/1993 |
| EP | 0 742 244 A2 | 11/1996 |
| EP | 0 785 194 A1 | 7/1997 |
| EP | 0 803 504 A2 | 10/1997 |
| EP | 0 942 027 A2 | 9/1999 |
| EP | 1 046 931 A2 | 10/2000 |
| FR | 1 602 277 A | 11/1970 |
| JP | 58-164615 | 9/1983 |
| JP | 04-058489 | 10/1985 |
| JP | 02-270859 | 11/1990 |
| JP | 06-005323 | 10/1991 |
| JP | 05-148340 | 6/1993 |
| JP | 07-118390 | 5/1995 |
| JP | 09-071580 | 3/1997 |
| JP | 09-110979 | 4/1997 |
| WO | WO 98/35955 | 8/1998 |

OTHER PUBLICATIONS

Tanaka et al, CA135:273668, 2001.*
Yoshimura et al, CA136:158587, 2002.*
Antropov et al, CA83:87408, 1975.*
Yoshimura, Yuichi et al., "thio compounds, their compositions, optical materials as lenses having high refractive index, and their manufacture," Jan. 8, 2003 (abstract).
Hallensleben, Manfred L., "Anionic copolymerization of cyclic disulfides with 2-nitropropene," *Makromolekulare Chemie*, 175(11), pp. 3315-3317 (1974).
English language Patent Abstract of JP 2001-163875 (Jun. 19, 2001).
English language Patent Abstract of JP 2000-256435 (Sep. 19. 2000).
English language Patent Abstract of JP 07-118390 (May 9, 1995).
English language Patent Abstract of JP 2003-002889 (Jan. 8, 2003).
International Search Report dated Jun. 6, 2003.
Burns, John A., et al. "Predicting the stability of cyclic disulfides by molecular modeling: effective concentrations in thiol-disulfide interchange and the design of strongly reducing dithiols," *Journal of the American Chemical Society*, 112(7), pp. 6296-6303 (1990) (abstract).

(Continued)

Primary Examiner—Deborah C. Lambkin
(74) Attorney, Agent, or Firm—Finnegan, Henderson, Farabow, Garrett & Dunner, LLP

(57) ABSTRACT

A compound capable of giving optical materials that may be high in both refractive index and Abbe's number and may be excellent in heat resistance and transparency, and a process that may produce the same with good efficiency are disclosed. The compound may be a cyclic disulfide compound including a structure represented by the following general formula (1) or (2) and having a sulfur content of from 50 to 85% by weight:

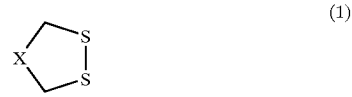

(1)

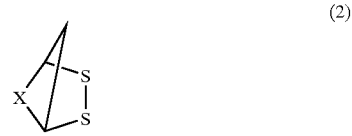

(2)

wherein X represents a chain having carbon and/or sulfur as a skeleton, inclusive of cyclic ones; and the number of elements constituting X is from 1 to 4.

20 Claims, No Drawings

OTHER PUBLICATIONS

Joergensen, Flemming S., et al. "cis-Disulfides. Photoelectron spectrum of a 6,7-dithiabicyclo [3.2.1]octane", *Tetrahedron Letters*, 24(3), pp. 319-322 (1983) (abstract).

Hallensleben, Manfred L., Copolymers from disulfide polymers and vinyl monomers by radical chains transfer, *European Polymer Journal*, 13(6), pp. 437-440 (1977) (abstract).

Chemical Concepts MS Database, Volatile Compounds in Food, 2nd Ed., Chemical Concepts GmbH, pp. 1-35 (see p. 5) 1999.

* cited by examiner

CYCLIC DISULFIDE COMPOUND, PROCESS OF PRODUCING THE SAME AND OPTICAL PRODUCT COMPRISING THE SAME

CROSS-REFERENCE TO RELATED APPLICATION

The present application claims priority under 35 U.S.C. § 119 of Japanese Application No. 2002-031293, filed Feb. 7, 2002, the disclosure of which is expressly incorporated by reference herein.

FIELD OF THE INVENTION

The present invention relates to cyclic disulfide compounds, cyclic disulfide intermediates, processes of producing the same, and optical products comprising the same. The invention relates to cyclic disulfide compounds capable of giving optical materials that are high in both refractive index and Abbe's number and are excellent in heat resistance and transparency, and to processes that may produce the same with good efficiency.

BACKGROUND OF THE INVENTION

In recent years, plastics have been used in various optical applications such as lenses because they are lightweight, difficult to break, and readily dyed as compared with glasses. Examples of optical plastic materials include poly(diethylene glycol bisallyl carbonate) (CR-39) and poly(methyl methacrylate). However, these plastics have a refractive index of 1.50 or less. Accordingly, for example, in the case where they are used as a lens material, when the diopter increases, the lens becomes thick, thereby reducing the advantage that plastics are lightweight. Especially in a powerful concave lens, the edge of the lens becomes thick so that birefringence or chromatic aberration is generated. In addition, in spectacles, thick lenses are usually not esthetic.

On the other hand, in order to obtain thin lenses, it is effective to increase the refractive index of the material. However, in general, in glasses and plastics, the Abbe's number decreases with an increase of the refractive index. As a result, their chromatic aberration increases. Accordingly, plastic materials having both a high refractive index and a high Abbe's number are demanded.

Examples of such plastic materials include (1) polyurethanes obtained by polyaddition of a polyol having bromine in the molecule thereof and a polyisocyanate (see JP-A-58-164615); and (2) polythiourethanes obtained by polyaddition of a polythiol and a polyisocyanate (see JP-B-4-58489 and JP-B-5-148340). The preferred polythiol as a starting material of the polythiourethanes (2) include branched chains having an increased amount of sulfur (see JP-A-2-270859 and JP-A-5-148340), and polythiols having a dithiane structure introduced thereinto for the purpose of increasing sulfur content (see JP-B-6-5323 and JP-A-7-118390). Further, there are proposed (3) alkyl sulfide polymers containing an episulfide as a polymerization functional group (see JP-A-9-71580 and JP-A-9-110979).

However, with respect to the polyurethanes (1), the refractive index is slightly improved, but there are defects such that the Abbe's number is low, the light resistance is inferior, the specific gravity is high, and the lightweight properties are reduced. Further, with respect to the polythiourethanes (2), those obtained by using a polythiol having a high sulfur content as the starting polythiol have, for example, an increased refractive index as high as from about 1.60 to 1.68, but in comparison with optical inorganic glasses having an equivalent refractive index, the Abbe's number is low, so that the Abbe's number must be further increased. Moreover, with respect to the alkyl sulfide polymers (3), as one example, when the Abbe's number is 36, the refractive index is increased to 1.70, so that lenses obtained by using such polymers may be remarkably thin and light in weight. However, plastic materials having further increased refractive index and Abbe's number are demanded.

SUMMARY OF THE INVENTION

In order to address the above-described problems, the invention was made. The invention provides compounds capable of giving optical materials that are high in both of refractive index and Abbe's number and are excellent in heat resistance and transparency, and processes that may produce the same with good efficiency, and optical products comprising the same.

The present inventors have determined that cyclic disulfide compounds containing a given structure and containing from 50 to 85% by weight of sulfur can address the above-described problems, and that these compounds can be produced with good efficiency.

The invention provides cyclic disulfide compounds containing a structure represented by the following general formula (1) or (2) and having a sulfur content of from 50 to 85% by weight:

wherein X represents a chain comprising carbon and/or sulfur as a skeleton, inclusive of cyclic ones; and the number of atoms constituting X is from 1 to 4. The invention also provides a process of producing this compound by reacting a polythiol having a plurality of mercapto groups with lead acetate and oxidizing the obtained lead dithiolate.

DESCRIPTION OF THE INVENTION

The particulars shown herein are by way of example and for purposes of illustrative discussion of the various embodiments of the present invention only. In this regard, no attempt is made to show details of the invention in more detail than is necessary for a fundamental understanding of the invention, the description making apparent to those skilled in the art how the several forms of the invention may be embodied in practice.

Unless otherwise stated, a reference to a compound or component, includes the compound or component by itself, as well as in combination with other compounds or components, such as mixtures of compounds.

The cyclic disulfide compounds according to the invention contain a structure represented by the following general formula (1) or (2) and contain from 50 to 85% by weight of sulfur.

(1)

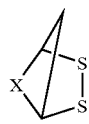
(2)

In the formulae, X represents a chain comprising carbon and/or sulfur as a skeleton, inclusive of cyclic ones; and the number of atoms constituting X is from 1 to 4.

These cyclic disulfide compounds contain sulfur having high atomic refraction in a relatively high proportion, thereby increasing the refractive index of its polymer. These compounds may form a linear disulfide chain through ring opening polymerization, and the linear disulfide chain also contributes to an increase of the refractive index. Usually, the Abbe's number of amorphous materials tends to decrease with an increase of their refractive index. In the case of polymers having sulfur in a high proportion, electron resonance of sulfur becomes remarkable, so that a large decrease of the Abbe's number is often observed. However, the cyclic disulfide compounds according to the invention are generally free from such phenomenon. The structure represented by the general formula (1) or (2) may be obtained by oxidizing a lead dithiolate that may be obtained by reacting a polythiol with lead acetate. In order to obtain the desired material in a good yield, X in the general formula (1) or (2) is generally a chain having from 1 to 4 carbons and/or sulfurs in total as a skeleton. When this range is exceeded, the cyclic disulfide compound according to the invention may not be obtained, or its yield may be lowered. A glass transition temperature (Tg) of a polymer obtained from the cyclic disulfide compound according to the invention generally decreases with an increase of this chain. Accordingly, in order to obtain polymers having good heat resistance, in addition to the restrictions in production as described above, the number of elements of X in the structure represented by the general formula (1) or (2) is generally from 1 to 4.

A plural number of different structures represented by the general formula (1) and/or (2) may be present in one molecule. For example, 1,1'-bi-2,4,5,7-tetrathiacycloheptane formed by the reaction of Scheme 2 as described below is a compound having two structures of the general formula (1) and falls within the scope of the invention.

The cyclic disulfide compound according to the invention has a structure of the general formula (1) or (2) and contains from 50 to 85% by weight of sulfur, and with respect to the substituent on X of the general formula (1) or (2), there are no limitations at all. Examples include monocyclic, polycyclic, spiro-cyclic, and fused-ring disulfides. Specific examples include 1,2-dithiacyclopentane, 1,2-dithiacyclohexane, 1,2,5-trithiacycloheptane, 1,2,4-trithiacyclopentane, 2-(1,2-di-thiacyclopentyl)sulfide, 2-(1,2-dithiacyclooctyl)disulfide, 1,1'-bi-2,4,5,7-tetrathiacycloheptane, bis(1,3,5,6-tetrathia-2-cycloheptyl)methane, 1,1'-bi-2,3,5-tri-thiolane, bicyclo[3.3.0]-2,3,6,7-tetrathiaoctane, and bicyclo[2.2.1]-2,3,5,6-tetrathiaheptane.

The production process of the cyclic disulfide compound according to the invention will be described in the following Scheme 1 as an example of the synthesis of bicyclo[2.2.1]-2,3,5,6-tetrathiaheptane.

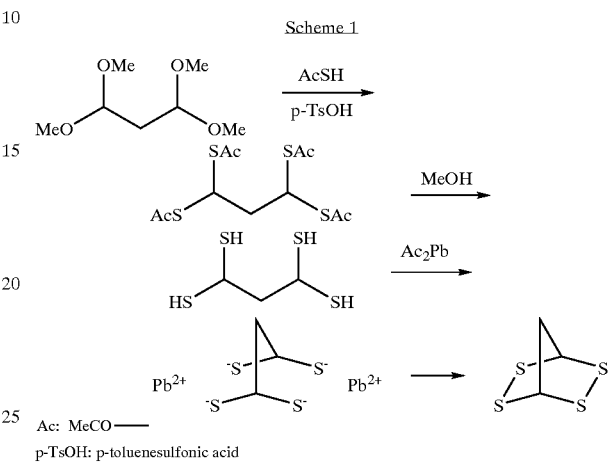

Scheme 1

Ac: MeCO—
p-TsOH: p-toluenesulfonic acid

Malonaldehyde bis(dimethyl acetal) is reacted with thioacetic acid at from room temperature to 80° C. in the presence of p-toluenesulfonic acid as a catalyst, to obtain tetrathioacetate. This compound may also be obtained by reaction of 1,1,3,3-tetrabromopropane and sodium thioacetate. In general, as the starting material of the thioacetate, an alkoxy acetal or a bromide may be selected taking into consideration the cost and the availability. The former is useful for the preparation of a gem-thioacetate, i.e., a compound in which two thioacetate groups are connected to the same carbon atom. The obtained thioacetate is subjected to methanolysis in the presence of an acid catalyst, to give a corresponding thiol. Examples of the acid catalyst include protonic acids such as hydrogen chloride, p-toluenesulfonic acid, and sulfuric acid. In addition to methanol, ethanol and propanol can be used for the solvolysis. Thioacetates other than the gem-thioacetate are hydrolyzed with an alkaline hydroxide aqueous solution, e.g., 5 or 10% NaOH (aq), and made acidic, e.g., by adding dilute HCl (aq), to give a corresponding thiol. Next, the thiol is reacted with an aqueous solution of lead acetate, thereby obtaining lead dithiolate substantially quantitatively. Since the lead dithiolate is formed such that the sulfur atom is partitioned by at least three carbon atoms, the lead dithiolate having a conformation shown in Scheme 1 is selectively obtained. The production process of the cyclic disulfide compound according to the invention is characterized in that by selective formation of the lead dithiolate as a precursor of the cyclic disulfide by the reactions shown in Scheme 1, that is, through an intermediate comprising the novel lead dithiolate, a stable cyclic disulfide having the structure of the general formula (1) or (2) exclusive of unstable dithiacyclopropane or 1,2-dithiacyclobutane can be produced with good efficiency. Finally, a benzene solution containing from 0.02 to 2 moles/L of this lead dithiolate is oxidized with an equivalent amount of sulfur, selenium, chlorine, or iodine, to obtain the desired cyclic disulfide compound. The production process of the cyclic disulfide compound according to the invention is also characterized in that an extremely diluted state for increasing the proportion of intramolecular reaction to give the cyclic disulfide is not required.

As an additional specific example, the production example of 1,1'-bi-2,4,5,7-tetrathiacycloheptane as a polycyclic disulfide will be described in the following Scheme 2.

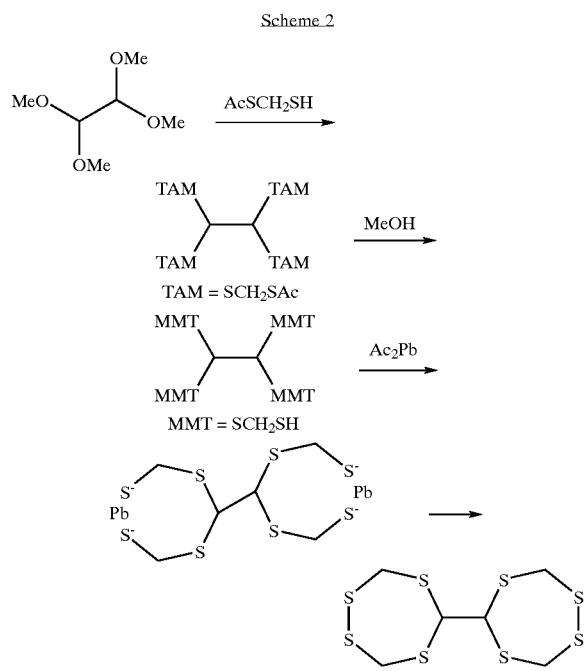

Glyoxal bis(dimethyl acetal) is reacted with mercapto acetylthiomethane, and the obtained thioacetyl derivative is subjected to methanolysis to obtain a tetrathiol. In both reactions, the acid catalyst described in detail in Scheme 1 can be used, such as p-toluenesulfonic acid. When a propanol solution of this tetrathiol is reacted with an aqueous solution of lead acetate trihydrate, bis(lead dithiolate) is instantly deposited and obtained. Finally, this bis(lead dithiolate) is oxidized to obtain the cyclic disulfide according to the invention. In this reaction, the oxidizing agent described in detail in Scheme 1 can also be used, such as iodine. In contrast with Scheme 1, this bis(lead dithiolate) was dispersed in benzene but oxidized in a high yield.

Next, the optical materials obtained by using the cyclic disulfide compound according to the invention will be described. The cyclic disulfide compound having the structure of the general formula (1) or (2) according to the invention is included in the optical material. The cyclic disulfide compound according to the invention may be used singly or in admixture of two or more thereof. Further, the cyclic disulfide compound can be mixed with other episulfide compounds, epoxy compounds, and vinyl monomers as components for improving physical properties of the obtained polymer and then used.

Examples of the episulfide compounds that may be used include chain organic compounds such as bis(β-epithiopropylthio)methane, 1,2-bis(β-epithiopropylthio)ethane, 1,3-bis(β-epithiopropylthio)propane, 1,2-(β-epithio-propylthio)propane, 1-(β-epithiopropylthio)-2-(β-epithiopropylthiomethyl)propane, 1,4-bis(β-epithiopropylthio)butane, 1,3-bis(β-epithiopropylthio)butane, 1-(β-epithiopropylthio)-3-(β-epithiopropylthiomethyl)butane, 1,5-bis(β-epithiopropylthio)pentane, 1-(β-epithiopropylthio)-4-(β-epithiopropylthiomethyl)pentane, 1,6-bis(β-epithiopropylthio)hexane, 1-(β-epithiopropylthio)-5-(β-epithiopropylthiomethyl)hexane, 1-(β-epithiopropylthio)-2-[(2β-epithiopropylthioethyl)thio]ethane, and 1-(β-epithiopropylthio)-2-[[2-(2-β-epithiopropylthioethyl)thioethyl]thio]ethane; branched organic compounds such as tetrakis(β-epithiopropylthiomethyl)methane, 1,1,1-tris(β-epithiopropylthiomethyl)propane, 1,5-bis(β-epithiopropylthio)-2-(β-epithiopropylthiomethyl)-3-thiapentane, 1,5-bis(β-epithiopropylthio)-2,4-bis(β-epithiopropylthiomethyl)-3-thiapentane, 1-(β-epithiopropylthio)-2,2-bis(β-epithiopropylthiomethyl)-4-thiahexane, 1,5,6-tris(β-epithiopropylthio)-4-(β-epithiopropylthiomethyl)-3-thiahexane, 1,8-bis(β-epithiopropylthio)-4-(β-epithiopropylthiomethyl)-3,6-dithiaoctane, 1,8-bis(β-epithiopropylthio)-4,5-bis(β-epithiopropylthiomethyl)-3,6-dithiaoctane, 1,8-bis(β-epithiopropylthio)-4,4-bis(β-epithiopropylthiomethyl)-3,6-dithiaoctane, 1,8-bis(β-epithiopropylthio)-2,4,5-tris(β-epithiopropylthiomethyl)-3,6-dithiaoctane, 1,8-bis(β-epithiopropylthio)-2,5-bis(β-epithiopropylthiomethyl)-3,6-dithiaoctane, 1,9-bis(β-epithiopropylthio)-5-(β-epithiopropylthiomethyl)-5-[(2-α-epithiopropylthioethyl)thiomethyl]-3,7-dithianonane, 1,10-bis(β-epithiopropylthio)-5,6-bis[(2-β-epithiopropylthioethyl)thio]-3,6,9-trithiadecane, 1,11-bis(β-epithiopropylthio)-4,8-bis(β-epithiopropylthiomethyl)-3,6,9-trithiaundecane, 1,1-bis(β-epithiopropylthio)-5,7-bis(β-epithiopropylthiomethyl)-3,6,9-trithiaundecane, 1,11-bis(β-epithiopropylthio)-5,7-[(2-β-epithiopropylthioethyl)thiomethyl]-3,6,9-trithiaundecane, and 1,11-bis(β-epithiopropylthio)-4,7-bis(β-epithiopropylthiomethyl)-3,6,9-trithiaundecane, and those compounds in which at least one hydrogen of the episulfide group thereof is substituted with a methyl group; cyclic aliphatic organic compounds such as 1,3- or 1,4-bis(β-epithiopropylthio)cyclohexane, 1,3- or 1,4-bis(β-epithiopropylthiomethyl)cyclohexane, bis[4-(β-epithiopropylthio)cyclohexyl]methane, 2,2-bis[4-(β-epithiopropylthio)cyclohexyl]propane, bis[4-(β-epithiopropylthio)cyclohexyl]sulfide, 2,5-bis(β-epithiopropylthiomethyl)-1,4-dithiane, and 2,5-bis(β-epithiopropylthioethylthiomethyl)-1,4-dithiane, and those compounds in which at least one hydrogen of the episulfide group thereof is substituted with a methyl group; and aromatic organic compounds such as 1,3- or 1,4-bis(β-epithiopropylthio)benzene, 1,3- or 1,4-bis(β-epithiopropylthiomethyl)benzene, bis[4-(β-epithiopropylthio)phenyl]methane, 2,2-bis[4-(β-epithiopropylthio)phenyl]propane, bis[4-(β-epithiopropylthio)phenyl]sulfide, bis[4-(β-epithiopropylthio)phenyl]sulfone, and 4,4'-bis(β-epithiopropylthio)biphenyl, and those compounds in which at least one hydrogen of the episulfide group thereof is substituted with a methyl group. These may be used singly or in admixture of two or more thereof. The amount of the episulfide compound to be used may be from 0.01 to 80% by mole based on the total amount of the cyclic disulfide compound according to the invention.

Examples of the epoxy compounds that may be used include phenol-based epoxy compounds produced by condensation of a polyhydric phenol compound such as hydroquinone, catechol, resorcin, bisphenol A, bisphenol F, bisphenol sulfone, bisphenol ether, bisphenol sulfide, a halogenated bisphenol A, and novolak resins and an epihalohydrin; alcohol-based epoxy compounds produced by condensation of a polyhydric alcohol compound such as ethylene glycol, diethylene glycol, triethylene glycol, polyethylene glycol, propylene glycol, dipropylene glycol, polypropylene glycol, 1,3-propanediol, 1,4-butanediol, 1,6-hexanediol, neopentyl glycol, glycerin, trimethylolpropane trimethacrylate, pentaerythritol, 1,3- or 1,4-cyclohexanediol, 1,3- or 1,4-cyclohexanedimethanol, hydrogenated bisphenol A, bisphenol A.ethylene oxide adduct, and bisphenol A.propylene oxide adduct and an epihalohydrin; glycidyl ester-based epoxy compounds produced by condensation of a polyhydric carboxylic acid such as adipic acid, sebacic acid, dodecanedicarboxylic acid, dimer acid, phthalic acid, isophthalic acid, terephthalic acid, tetrahydrophthalic acid, methyltetrahydrophthalic acid, hexahydrophthalic acid, hexahydroisophthalic acid, hexahydroterephthalic acid, hexachloroendomethylene tetrahydrophthalic ("HET") acid, nadic acid, maleic acid, succinic acid, fumaric acid, trimellitic acid, benzenetetracarboxylic acid, benzo-phenonetetracarboxylic acid, naphthalenedicarbxoylic acid, and diphenyldicarboxylic acid and an epihalohydrin; amine-based epoxy compounds produced by condensation of a primary diamine such as ethylenediamine, 1,2-diaminopropane, 1,3-diaminopropane, 1,2-diaminobutane, 1,3-diaminobutane, 1,4-diaminobutane, 1,5-diaminopentane, 1,6-diaminohexane, 1,7-diaminoheptane, 1,8-diaminooctane, bis-(3-aminopropyl)ether, 1,2-bis-(3-aminopropoxy)ethane, 1,3-bis-(3-aminopropoxy)-2,2'-dimethylpropane, 1,2-, 1,3- or 1,4-bisaminocyclohexane, 1,3- or 1,4-bisaminomethylcyclohexane, 1,3- or 1,4-bisaminoethylcyclohexane, 1,3- or 1,4-bisaminopropylcyclohexane, hydrogenated 4,4'-diaminodiphenylmethane, isophoronediamine, 1,4-bisaminopropylpiperazine, m- or β-phenylenediamine, 2,4- or 2,6-tolylenediamine, m- or p-xylylenediamine, 1,5- or 2,6-naphthalenediamine, 4,4'-diaminodiphenylmethane, 4,4'-diaminodiphenyl ether, and 2,2-(4,4'diaminodiphenyl)propane or a secondary diamine such as N,N'-dimethylethylenediamine, N,N'-dimethyl-1,2-diaminopropane, N,N'-dimethyl-1,3-diaminopropane, N,N'-dimethyl-1,2-diaminobutane, N,N'-dimethyl-1,3-diaminobutane, N,N'-dimethyl-1,4-diaminobutane, N,N'-dimethyl-1,5-diaminopentane, N,N'-dimethyl-1,6-diaminohexane, N,N'-dimethyl-1,7-diaminoheptane, N,N'-diethylethylenediamine, N,N'-diethyl-1,2-diaminopropane, N,N'-diethyl-1,3-diaminopropane, N,N'-diethyl-1,2-diaminobutane, N,N'-diethyl-1,3-diaminobutane, N,N'-diethyl-1,4-diaminobutane, N,N'-diethyl-1,6-diaminohexane, piperazine, 2-methylpiperazine, 2,5- or 2,6-dimethylpiperazine, homopipirazine, 1,1-di-(4-piperizyl)-methane, 1,2-di-(4-piperizyl)-ethane, 1,3-di-(4-piperizyl)-propane, and 1,4-di-(4-piperizyl)-butane and an epihalohydrin; alicyclic epoxy compounds such as 3,4-epoxycyclohexyl-3,4-epoxycyclohexanecarboxylate, vinylcyclohexane dioxide, 2-(3,4-epoxycyclohexyl)-5,5-spiro-3,4-epoxycyclohexane-meta-dioxane, and bis(3,4-epoxycyclohexyl)adipate; epoxy compounds produced by epoxidation of an unsaturated compound, such as cyclopentadiene epoxide, epoxidized soybean oil, epoxidized polybutadiene, and vinylcyclohexene epoxide; and urethane-based epoxy compounds produced from the foregoing polyhydric alcohols or phenol compounds, and a diisocyanate or glycidol. These may be used singly or in admixture of two or more thereof. The amount of the epoxy compound to be used may be from 0.01 to 80% by mole based on the total amount of the cyclic disulfide compound according to the invention.

Examples of the vinyl monomers that may be used include compounds having an ester structure of a monohydric or polyhydric alcohol and acrylic acid or methacrylic acid, such as methyl acrylate, methyl methacrylate, ethyl acrylate, ethyl methacrylate, ethylene glycol diacrylate, ethylene glycol dimethacrylate, diethylene glycol diacrylate, diethylene glycol dimethacrylate, triethylene glycol diacrylate, triethylene glycol dimethacrylate, polyethylene glycol diacrylate, polyethylene glycol dimethacrylate, 1,3-butylene glycol diacrylate, 1,3-butylene glycol dimethacrylate, 1,6-hexanediol diacrylate, 1,6-hexanediol dimethacrylate, neopentyl glycol diacrylate, neopentyl glycol dimethacrylate, polypropylene glycol diacrylate, polypropylene glycol dimethacrylate, 2,2-bis[4-(acryloxyethoxy)phenyl]propane, 2,2-bis[4-(methacryloxyethoxy)phenyl]propane, 2,2-bis[4-(acryloxy.diethoxy)phenyl]propane, 2,2-bis[4-(methacryloxy.diethoxy)phenyl]propane, 2,2-bis[4-(acryloxy.polyethoxy)phenyl]propane, 2,2-bis[4-(methacryloxy.polyethoxy)phenyl]propane, trimethylolpropane triacrylate, trimethylolpropane trimethacrylate, pentaerythritol tetraacrylate, pentaerythritol tetra-methacrylate, hexaacrylate of bis(2,2,2-trimethylolethyl)ether, and hexamethacrylate of bis(2,2,2-trimethylolethyl)ether; allyl compounds such as allyl sulfide, diallyl phthalate, and diethylene glycol bisallyl carbonate; vinyl compounds such as acrolein, acrylonitrile, and vinyl sulfide; and aromatic vinyl compounds such as styrene, α-methylstyrene, methylvinylbenzene, ethylvinylbenzene, α-chlorostyrene, chlorovinylbenzene, vinylbenzyl chloride, p-divinylbenzene, and m-divinylbenzene. These may be used singly or in admixture of two or more thereof. The amount of the vinyl monomer to be used may be from 0.01 to 20% by mole based on the total amount of the cyclic disulfide compound according to the invention.

So far as the invention is not hindered, if desired, additives for the purpose of improving weather resistance, such as ultraviolet light absorbers, antioxidants, coloration inhibitors, and fluorescent dyes, may be added to the polymerizable composition of the invention. Further, in order to enhance the polymerization reaction, a catalyst may be used. For example, amines, phosphines, lithium, sodium or potassium salts of thiols and crown ether complexes thereof, quaternary ammonium salts, quaternary phosphonium salts, tertiary sulfonium salts, secondary iodonium salts, mineral acids, Lewis acids, organic acids, silicates, and tetrafluoroborates are effective.

The optical materials obtained by using the cyclic disulfide compound according to the invention are produced by, for example, the following method.

First of all, a uniform composition containing the above-described polymerizable composition and various additives that are used as the need arises is prepared. Next, this composition is poured into a mold in which a glass- or metal-made mold is combined with a resin-made gasket and heat cured using a casting polymerization process. At this time, in order to make it easy to take out the resin after molding, the mold may be previously subjected to release processing, or the composition may be mixed with a releasing agent. The polymerization temperature varies depending upon the compound to be used but is generally from –20 to +150° C., and the polymerization time is generally from about 0.5 to 72 hours. The polymer released from the mold after the polymerization can be dyed in water or an organic solvent by using a usual disperse dye. At this time, in order to make the dyeing easier, a carrier may be added to the dye dispersion, or heating may be applied. The thus obtained optical materials are not limited thereto, but may be used as optical products such as plastic lenses.

The cyclic disulfide compound according to the invention is a polymerizable disulfide cyclically bound, such as with three or more carbons or carbons and sulfurs, and is suitably used as a starting material for optical materials. Further, since optical materials obtained by using the cyclic disulfide compound according to the invention may have a high refractive index and a high Abbe's number and may be excellent in heat resistance and transparency, they are suitable as materials for the preparation of optical products such as lenses for spectacles and cameras, prisms, optical fibers, recording medium substrates for optical discs and magnetic discs, colored filters, and infrared light absorption filters.

The present invention will be further illustrated by way of the following Examples. These Examples are non-limiting and do not restrict the scope of the invention.

EXAMPLES

The physical properties of the cyclic disulfides obtained in the Examples and the physical properties of the polymers obtained in the Application Examples and Comparative Application Examples were measured by the following methods:

1) Refractive index ($n_D$) and Abbe's number ($v_D$): Measured at 25° C. using an Abbe's refractometer, DR-M4 produced by Atago Co., Ltd.
2) Appearance: Visually observed.
3) Heat resistance: Carried out TMA measurement under a load of 98 mN (10 gf) using a 0.5 mmϕ-pin by a Rigaku TMA device produced by Rigaku International Corporation, and evaluated from a peak temperature of a chart obtained by a temperature elevation at a rate of 10° C./min.
4) Transparency: Evaluated at a light transmittance of 550 nm using a ultraviolet light spectrometer, UV-330 produced by Hitachi, Ltd.

Example 1

Production Example of Bicyclo[2.2.1]-2.3,5,6-Tetrathiaheptane

A mixture of malonaldehyde bis(dimethyl acetal) (16.4 g), thioacetic acid (33.5 g), and p-toluenesulfonic acid monohydrate (1.9 g) was heated at 60° C. for 4 hours under a reduced pressure of 1 kPa until methanol did not distill out. The reaction mixture was cooled to room temperature and then dissolved in methanol (200 mL) containing 2% of hydrogen chloride, and the solution was stirred at room temperature for 24 hours. The reaction mixture was poured into ice water and extracted with chloroform, and the solvent was distilled off, to obtain 1,1,3,3-tetramercaptopropane. To a methanol (100 mL) solution of this thiol was added an aqueous solution (200 mL) of lead acetate trihydrate (75.9 g), and an instantly deposited precipitate was separated by filtration, washed with water, and then dried. The obtained lead dithiolate was dispersed in benzene (1 L), sulfur (6.4 g) was added thereto, and the mixture was stirred at room temperature for 2 hours. The reaction mixture from which deposited lead sulfide had been separated by filtration was distilled under 267 Pa at 92° C., to obtain the desired material with an overall yield of 64%. This compound had a refractive index ($n_D$) of 1.692 and an Abbe's number ($v_D$) of 33.1.

The analysis results for identifying the structure of this compound are given below.

$^1$H-NMR (solvent: $CDCl_3$, internal standard substance: TMS): d3.43 (d, 2H), d4.12 (t, 2H). Elemental analysis values (calculated values): C; 21.5% (21.4%), H; 2.43% (2.38%), S; 75.7% (76.2%).

Example 2

Production Example of 1,1'-BI-2,5,7-Tetrathiacycloheptane

A mixture of glyoxal bis(dimethyl acetal) (15 g), mercapto acetylthiomethane (48.9 g), and p-toluenesulfonic acid monohydrate (1.9 g) was heated at 60° C. for 6 hours under a reduced pressure of 1 kPa until methanol did not distill out. This reaction mixture was dissolved in methanol (200 mL), and the solution was stirred at 60° C. for 4 hours. The reaction mixture was poured into ice water and extracted with chloroform, and the solvent was distilled off, to obtain 1,1,2,2-tetrakis(mercapto methylthio)ethane. To a propanol (100 mL) solution of this thiol was added an aqueous solution (200 mL) of lead acetate trihydrate (75.9 g), and an instantly deposited precipitate was separated by filtration, washed with water, and then dried. The obtained lead dithiolate was dispersed in benzene (1 L), iodine (50.8 g) was added thereto, and the mixture was stirred at room temperature for 3 hours. Deposited lead iodide was separated by filtration, and the benzene solution was washed with a 5% sodium hydrogensulfite aqueous solution and water, and then dried. The benzene was removed to obtain the desired material with an overall yield of 54%. This compound had a refractive index ($n_D$) of 1.711 and an Abbe's number ($v_D$) of 32.4.

The analysis results for identifying the structure of this compound are given below.

$^1$H-NMR (solvent: $CDCl_3$, internal standard substance: TMS): d4.53 (d, 2H), d5.52 (s, 8H). Elemental analysis values (calculated values): C; 20.8% (21.3%), H; 3.01% (2.95%), S; 75.7% (75.8%).

Example 3

Production Example of Bicyclo[3.3.0]-2.3,6,7-Tetrathiaoctane

A dispersion mixture of 1,2,3,4-tetrabromobutane (37.4 g) and potassium thioacetate (45.7 g) in anhydrous ethanol (200 mL) was refluxed for 30 minutes, and after cooling to room temperature, a 40% potassium hydroxide aqueous solution (61.7 g) was added thereto, followed by stirring at room temperature for 2 hours. The reaction mixture was made acidic to a pH of 3 to 4 with adequate concentrated hydrochloric acid, and the mixture was washed with water until the benzene extract became neutral, followed by drying. To an ethanol (100 mL) solution of a residue from which the benzene had been distilled out was added an aqueous solution (200 mL) of lead acetate trihydrate (75.9 g), and an instantly deposited precipitate was separated by filtration, washed with water, and then dried. The obtained lead dithiolate was dispersed in benzene (1 L), sulfur (6.4 g) was added thereto, and the mixture was stirred at room temperature for 3 hours. The reaction mixture from which deposited lead sulfide had been separated by filtration was distilled under 267 Pa at 86° C., to obtain the desired material with an overall yield of 44%. This compound had a refractive index ($n_D$) of 1.688 and an Abbe's number ($v_D$) of 33.9.

The analysis results for identifying the structure of this compound are given below.

$^1$H-NMR (solvent: $CDCl_3$, internal standard substance: TMS): d5.32 (m, 2H), d3.48 (dd, 4H). Elemental analysis values (calculated values): C; 26.1% (26.3%), H, 3.3% (3.29%), S; 75.7% (75.4%).

Application Example 1

Production of Optical Material Comprising Polymer

A mixture of 0.1 moles of bicyclo[2.2.1]-2,3,5,6-tetrathiaheptane (CD1) from Example 1 and $2 \times 10^{-5}$ moles of triethylamine (CT1) as a polymerization catalyst was uniformly stirred at 60° C., poured into two glass molds for molding lenses, and heat polymerized at 70° C. for 10 hours, at 80° C. for 5 hours, and then at 100° C. for 3 hours, to obtain a lens-shaped polymer. Various physical properties of the obtained polymer are shown in Table 1. It can be understood from Table 1 that the polymer obtained in this Application Example 1 was colorless and transparent, had a very high refractive index ($n_D$) as high as 1.811, had a very high Abbe's number ($v_D$) as high as 30 (lowly dispersed), and was excellent in heat resistance (125° C.) and transparency (92%). Accordingly, the obtained polymer was suitable as an optical material.

Application Examples 2 to 5

Production of Optical Materials Comprising Polymer

Using the cyclic disulfide compound according to the invention, an episulfide compound, an epoxy compound and/or a vinyl monomer, and a polymerization catalyst as shown in Table 1, lens-shaped polymers were obtained in the same manner as in Application Example 1, except for changing the comonomers, catalyst, etc., as shown in Table 1. Various physical properties of the obtained polymers are shown in Table 1. It can be understood from Table 1 that the polymers obtained in Application Examples 2 to 5 were colorless and transparent, had a very high refractive index ($n_D$) as high as from 1.801 to 1.775, had a very high Abbe's number ($v_D$) as high as from 31 to 34 (lowly dispersed), and were excellent in heat resistance (104 to 138° C.) and transparency (89 to 96%).

Comparative Application Example 1

Production of Optical Material Comprising Polymer

A mixture of 0.1 moles of pentaerythritol tetrakismercapto propionate (CE1), 0.2 moles of m-xylylene diisocyanate (CE2), and $1.0 \times 10^{-4}$ moles of dibutyltin dichloride (CT4) as shown in Table 2 was uniformly stirred, poured into two glass molds for molding lenses, and heat polymerized at 50° C. for 10 hours, at 60° C. for 5 hours, and then at 120° C. for 3 hours, to obtain a lens-shaped polymer. Various physical properties of the obtained polymer are shown in Table 2. It can be understood from Table 2 that though the polymer obtained in this Comparative Application Example 1 was colorless and good in transparency (92%), it was low in $n_D/v_D$ (as high as 1.59/36) and poor in heat resistance (as high as 86° C.).

Comparative Application Examples 2 and 3

Production of Optical Materials Comprising Polymer

Lens-shaped polymers were obtained in the same manner as in Comparative Application Example 1, except for using each of the starting compositions as shown in Table 2. Various physical properties of the obtained polymers are shown in Table 2. It can be understood from Table 2 that the polymer of Comparative Application Example 2 was low in $n_D/v_D$ (as high as 1.67/28) and relatively good in heat resistance (94° C.), but was colored and was low in transparency (81%); and that the polymer of Comparative Application Example 3 had a relatively high $v_D$ (as high as 36), excellent in weather resistance, colorless, and good in transparency (89%), but was poor in heat resistance (90° C.) and had a not so high $n_D$ (1.70), and the polymer was brittle.

TABLE 1

| Appl. Example | Monomer component (mole) | Polymerization catalyst (mole) | $n_D/v_D$ | Appearance | Heat resist. (° C.) | Transparency (%) |
|---|---|---|---|---|---|---|
| 1 | CD1[*1] (0.1) | CT1[*11] ($2 \times 10^{-5}$) | 1.811/30 | Colorless and transparent Rigid | 125 | 92 |
| 2 | CD2[*2]/EP1[*4] (0.07/0.03) | CT1[*11] ($2 \times 10^{-5}$) | 1.792/31 | Colorless and transparent Rigid | 113 | 96 |
| 3 | CD3[*3]/EP2[*5] (0.05/0.05) | CT2[*12] ($4 \times 10^{-4}$) | 1.775/34 | Colorless and transparent Rigid | 104 | 91 |
| 4 | CD1[*1]/V[*6] (0.085/0.015) | CT3[*13] ($6 \times 10^{-5}$) | 1.801/31 | Colorless and transparent Rigid | 138 | 90 |
| 5 | CD1[*1]/CD3[*3]/ASD[*7] (0.06/0.02/0.02) | CT2[*12] ($6 \times 10^{-5}$) | 1.778/31 | Colorless and transparent Rigid | 115 | 89 |

[*1]CD1: Bicyclo[2.2.1]-2,3,5,6-tetrathiaheptane
[*2]CD2: 1,1'-Bi-2,4,5,7-tetrathiacycloheptane
[*3]CD3: Bicyclo[3.3.0]-2,3,6,7-tetrathiaoctane
[*4]EP1: Bis(epithiomethyl) sulfide
[*5]EP2: Bis(epithiomethyl) disulfide
[*6]V: 2,5-Bis(vinylthiomethyl)-1,4-dithiane
[*7]ASD: 1,7-Diepithio-2,3,5,6-tetrathiaheptane
[*11]CT1: Triethylamine
[*12]CT2: Boron trifluoride ethyl ether complex
[*13]CT3: Sodium thiophenolate, 18-crown-6 complex

TABLE 2

| Comp. Appl. Example | Monomer component (mole) | Polymerization catalyst (mole) | $n_D/v_D$ | Appearance | Heat resist. (° C.) | Transparency (%) |
|---|---|---|---|---|---|---|
| 1 | CE1[*8]/CE2[*9] (0.1/0.2) | CT4[*14] (1.0 × 10⁻⁴) | 1.59/36 | Colorless and transparent Rigid | 86 | 92 |
| 2 | CE3[*10]/CE2[*9] (0.2/0.3) | CT4[*14] (1.0 × 10⁻⁴) | 1.67/28 | Pale yellow and transparent | 94 | 81 |
| 3 | EP1[*4] (0.1) | CT1[*11] (1.0 × 10⁻⁴) | 1.70/36 | Colorless and transparent Brittle | 90 | 89 |

[*4]EP1: Bis(epithiomethyl) sulfide
[*8]CE1: Pentaerythritol tetrakismercapto propionate
[*9]CE2: m-Xylylene diisocyanate
[*10]CE3: 1,3,5-Trimercapotobenzene
[*11]CT1: Triethylamine
[*14]CT4: Dibutyltin dichloride While the invention has been described in connection with certain embodiments so that aspects thereof may be more fully understood and appreciated, it is not intended to limit the invention to these particular embodiments. On the contrary, it is intended to cover all alternatives, modifications and equivalents as may be included within the scope of the invention as defined by the appended claims.

What is claimed is:

1. A cyclic disulfide compound selected from a bicycle [2.2.1]-2,3,5,6-tetrathiapentane, a 1,1'-bi-2,4,5,7-tetrathiacyclohentane and a bicycle[3.3.0]-2,3,6,7-tetrathioctane

(1)

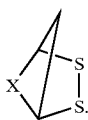

(2)

2. A process of producing a cyclic disulfide compound having a structure represented by the following general formula (1) or (2) and having a sulfur content of from 50 to 85% by weight:

(1)

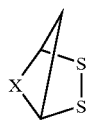

(2)

wherein X represents a chain comprising at least one of carbon and sulfur as a skeleton, the number of atoms constituting X is from 1 to 4, X is substituted or unsubstituted, and X optionally forms a ring separate from those shown in formulas (1) and (2); and with the proviso that 1,2-dithiacyclopentane is excluded comprising:

reacting a polythiol having a plurality of mercapto groups with lead acetate to obtain a lead dithiolate; and
  oxidizing the lead dithiolate to obtain the cyclic disulfide compound of the following general formula (1) or (2).

3. The process of claim 2 wherein X represents a chain comprising sulfur as a skeleton.

4. An optical product comprising a polymer obtainable by using, as a monomer component, a cyclic disulfide compound selected from a bicycle[2.2.1]-2,3,5,6-tetrathiapentane, a 1,1'-bi-2,4,5,7-tetrathiacyclohentane and a bicycle [3.3.0]-2,3,6,7-tetrathioctane.

(1)

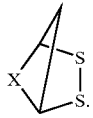

(2)

5. The optical product of claim 4, wherein the polymer is obtainable by using, as monomer components, the cyclic disulfide compound and an episulfide compound.

6. The optical product of claim 4, wherein the polymer is obtainable by using, as monomer components, the cyclic disulfide compound and an epoxy compound.

7. The optical product of claim 4, wherein the polymer is obtainable by using, as monomer components, the cyclic disulfide compound and a vinyl monomer.

8. The optical product of claim 4, wherein the optical product is a plastic lens.

9. The optical product of claim 5, wherein the optical product is a plastic lens.

10. The optical product of claim 6, wherein the optical product is a plastic lens.

11. The optical product of claim 7, wherein the optical product is a plastic lens.

12. The optical product of claim 4, wherein the optical product comprises spectacles.

13. The optical product of claim 4, wherein the optical product comprises a camera.

14. The optical product of claim 4, wherein the optical product comprises a prism.

15. The optical product of claim 4, wherein the optical product comprises optical fiber.

16. The optical product of claim 4, wherein the optical product comprises an optical disc.

17. The optical product of claim 4, wherein the optical product comprises a magnetic disc.

18. The optical product of claim 4, wherein the optical product comprises a colored filter.

19. The optical product of claim 4, wherein the optical product comprises an infrared light absorption filter.

20. A polymer obtainable by using, as a monomer component, a cyclic disulfide compound selected from a bicycle [2.2.1]-2,3,5,6-tetrathiapentane, a 1,1'-bi-2,4,5,7-tetrathiacyclohentane and a bicycle[3.3.0]-2,3,6,7-tetrathiaoctane

(1)

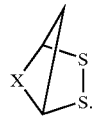

(2)

* * * * *